United States Patent
Althoff et al.

(10) Patent No.: US 10,559,387 B2
(45) Date of Patent: Feb. 11, 2020

(54) SLEEP MONITORING FROM IMPLICITLY COLLECTED COMPUTER INTERACTIONS

(71) Applicant: Microsoft Technology Licensing, LLC, Redmond, WA (US)

(72) Inventors: Tim Althoff, Rhineland-Palatinate (DE); Eric J. Horvitz, Kirkland, WA (US); Ryen W. White, Woodinville, WA (US)

(73) Assignee: Microsoft Technology Licensing, LLC, Redmond, WA (US)

(*) Notice: Subject to any disclaimer, the term of this patent is extended or adjusted under 35 U.S.C. 154(b) by 121 days.

(21) Appl. No.: 15/623,101

(22) Filed: Jun. 14, 2017

(65) Prior Publication Data
US 2018/0365384 A1   Dec. 20, 2018

(51) Int. Cl.
*G16H 50/00*   (2018.01)
*G16H 50/30*   (2018.01)
(Continued)

(52) U.S. Cl.
CPC ........... *G16H 50/30* (2018.01); *A61B 5/0077* (2013.01); *A61B 5/1123* (2013.01); *A61B 5/162* (2013.01);
(Continued)

(58) Field of Classification Search
CPC ..... G16H 50/20; A61B 5/0077; A61B 5/1123; A61B 5/162; A61B 5/4803; A61B 5/4815;
(Continued)

(56) References Cited

U.S. PATENT DOCUMENTS

| 7,766,827 B2* | 8/2010 | Balkin | A61B 5/16 600/300 |
| 8,428,993 B2* | 4/2013 | Lee | G06Q 10/06 705/7.13 |

(Continued)

FOREIGN PATENT DOCUMENTS

WO   WO-2016/154658 A1   10/2016

OTHER PUBLICATIONS

"American Time Use Survey", [Online]. U.S. Bureau of Labor Statistics. Retrieved from the Internet: <URL: http://www.webcitation.org/6IPcEntyS>, (2014), 2 pgs.
(Continued)

*Primary Examiner* — Carl H Layno
*Assistant Examiner* — Michael J Lau
(74) *Attorney, Agent, or Firm* — Schwegman Lundberg & Woessner, P.A.

(57) ABSTRACT

A method may include receiving implicitly collected computer interaction data of a user from a computing device; accessing a data store of previously collected computer interaction data, the previously collected computer interaction data correlated with sleep patterns of users; comparing the users implicitly collected computer interaction data to the previously collected computer interaction data; and inferring the user's sleep pattern based on the comparing. The method may provide an indication of real-world cognitive performance that varies throughout the day, and which is influenced by both circadian rhythms, chronotype (morning/evening preference), and prior sleep duration and timing.

20 Claims, 6 Drawing Sheets

(51) Int. Cl.
*G16H 50/20* (2018.01)
*A61B 5/00* (2006.01)
*A61B 5/11* (2006.01)
*A61B 5/16* (2006.01)
*G06F 19/00* (2018.01)

(52) U.S. Cl.
CPC ............ *A61B 5/4803* (2013.01); *A61B 5/486* (2013.01); *A61B 5/4815* (2013.01); *A61B 5/6897* (2013.01); *A61B 5/7278* (2013.01); *A61B 5/7435* (2013.01); *A61B 5/7475* (2013.01); *G06F 19/321* (2013.01); *G16H 50/20* (2018.01)

(58) Field of Classification Search
CPC ..... A61B 5/486; A61B 5/6897; A61B 5/7278; A61B 5/7435; A61B 5/7475; G06F 19/321
USPC ........................................................ 600/301
See application file for complete search history.

(56) References Cited

U.S. PATENT DOCUMENTS

| | | | | |
|---|---|---|---|---|
| 9,055,905 | B2* | 6/2015 | Watkins | A61B 5/18 |
| 9,189,596 | B2* | 11/2015 | Chen | A61B 5/16 |
| 2005/0177066 | A1* | 8/2005 | Aharonson | A61B 5/162 600/559 |
| 2007/0106624 | A1 | 5/2007 | Taylor et al. | |
| 2009/0005654 | A1* | 1/2009 | Jung | A61B 5/1101 600/300 |
| 2010/0076274 | A1* | 3/2010 | Severson | A61B 5/16 600/300 |
| 2011/0224510 | A1* | 9/2011 | Oakhill | G16H 50/30 600/301 |
| 2013/0243208 | A1* | 9/2013 | Fawer | A61B 5/162 381/57 |
| 2014/0085077 | A1* | 3/2014 | Luna | G08B 6/00 340/539.11 |
| 2014/0370479 | A1* | 12/2014 | Gazzaley | A61B 5/162 434/322 |
| 2015/0112899 | A1* | 4/2015 | Dagum | A61B 5/6898 706/12 |
| 2015/0120018 | A1* | 4/2015 | Wisbey | G16H 20/10 700/91 |
| 2015/0140527 | A1* | 5/2015 | Gilad-Barach | A61B 5/165 434/236 |
| 2015/0164418 | A1 | 6/2015 | Johnson et al. | |
| 2015/0272504 | A1* | 10/2015 | Giancardo | A61B 5/7267 600/595 |
| 2015/0297140 | A1* | 10/2015 | Hernandez | A61B 5/6897 600/547 |
| 2016/0051185 | A1* | 2/2016 | Wisbey | A61B 5/02438 705/2 |
| 2016/0063214 | A1* | 3/2016 | Blue | G06F 16/2237 705/3 |
| 2016/0164419 | A1* | 6/2016 | Chin | H02M 3/33507 363/21.16 |
| 2016/0196765 | A1 | 7/2016 | Stauch et al. | |
| 2016/0196785 | A1* | 7/2016 | Amesz | G02F 1/167 345/690 |
| 2016/0262680 | A1* | 9/2016 | Martucci | A61B 5/162 |
| 2017/0055899 | A1* | 3/2017 | Bandyopadhyay | A61B 5/4815 |

OTHER PUBLICATIONS

"Sleep disorders and sleep deprivation: An unmet public health problem", Report Brief, The National Academies, (Apr. 2006), 1-4.
Abdullah, Saeed, et al., "Cognitive Rhythms: Unobtrusive and Continuous Sensing of Alertness Using a Mobile Phone", Proceedings of the ACM International Joint Conference on Pervasive and Ubiquitous Computing (UBICOMP '16), Sep. 12-16, 2016, Heidelberg, German, (2016), 178-189.
Achermann, Peter, et al., "Simulation of daytime vigilance by the additive interaction of a homeostatic and a circadian process", Biological Cybernetics, 71(2), (Jun. 1994), 115-121.
Akerstedt, Torbjorn, et al., "The Three-Process Model of Alertness and its Extension to Performance, Sleep Latency, and Sleep Length", Journal of Chronobiology International, 14(2), (Mar. 1997), 115-123.
Alhola, Paula, et al., "Sleep deprivation: Impact on cognitive performance", Journal of Neuropsychiatric Disease and Treatment, 3(5), (Oct. 2007), 553-567.
Althoff, Tim, et al., "Influence of Pokemon Go on Physical Activity: Study and Implications", arXiv:1610.02085v2 [cs.CY] Oct. 28, 2016, Proceedings of Computer Research Repository, (Oct. 2016), 10 pgs.
Althoff, Tim, et al., "Large-Scale Analysis of Counseling Conversations: An Application of Natural language Processing to Mental Health", Proceedings of Transactions of the Association for Computational Linguistics, vol. 4, (2016), 463-476.
Althoff, Tim, et al., "Population-Scale Study of Sleep and Performance", [Online]. [Retrieved on Dec. 6, 2016]. Retrieved from the Internet: <URL: http://stanford.io/2ejFPhD, (2016), 12 pgs.
Ancoli-Israel, Sonia, et al., "The Role of Actigraphy in the Study of Sleep and Circadian Rhythms", Sleep, 26(3), (May 1, 2003), 342-392.
Basner, Mathias, et al., "American Time Use Survey: Sleep Time and its Relationship to Waking Activities", Sleep, 30(9), (2007), 1085-1095.
Blatter, Katharina, et al., "Circadian rhythms in cognitive performance: Methodological constraints, protocols, theoretical underpinnings", Physiology & Behaviour, vol. 90, Issue 2-3, (2007), 196-208.
Bohmer, Matthias, et al., "Falling Asleep with Angry Birds, Facebook and Kindle—A Large Scale Study on Mobile Application Usage", Proceedings of the 13th International Conference on Human Computer Interaction with Mobile Devices and Services (MobileHCI 2011, Aug. 30-Sep. 2, 2011, Stockholm, Sweden, (2011), 47-56.
Card, Stuart K., et al., "The keystroke-level model for user performance time with interactive systems", Communications of the ACM, vol. 23, Issue 7, (Jul. 1980), 396-410.
Dijk, Derk-Jan, et al., "Circadian and sleep/wake dependent aspects of subjective alertness and cognitive performance", Journal of Sleep Research, 1(2), (Jun. 1992), 112-117.
Dijk, Derk-Jan, et al., "Contribution of the Circadian Pacemaker and the Sleep Homeostat to Sleep Propensity, Sleep structure, Electroencephalographic Slow Waves, and Sleep Spindle Activity in Humans", Journal of Neuroscience, 15(5), (May 1995), 3526-3538.
Dinges, David F., "An overview of sleepiness and accidents", Journal of Sleep Research, vol. 4 (Suppl.), (Dec. 1995), 4-14.
Dinges, David F., "Chapter 12—Are You Awake? Cognitive Performance and Reverie During the Hypnopompic State", In: Sleep and Cognition, Bootzin, R. R., et al., Editors, Washington, DC, (1990), 159-175.
Dou, Zhicheng, et al., "A Large-Scale Evaluation and Analysis of Personalized Search Strategies", Proceedings of the 16th International Conference on World Wide Web (WWW 2007, May 8-12, 2007, Banff, Alberta, Canada, (2007), 581-590.
Fernandez-Mendoza, Julio, et al., "Insomnia with Objective Short Sleep Duration is Associated with Deficits in Neuropsychological Performance: A General Population Stutdy", Sleep, 33(4), (Apr. 2010), 459-465.
Golder, Scott A., et al., "Diurnal and Seasonal Mood Vary with Work, Sleep, and Daylength Across Diverse Cultures", Science, 333(6051), (2011), 1878-1881.
Hemp, Paul, "Presenteeism: At Work-But Out of It", Journal of Harvard Business Review, 82(1), (Oct. 2004), 49-58.
Juda, Myriam, et al., "Chronotype Modulates Sleep Duration, Sleep Quality,and Social Jet Lag in Shift-Workers", Journal of Biological Rhythms, 28(2), (Apr. 2013), 141-151.
Kelley, Paul, et al., "Synchronizing education to adolescent biology: 'let teens sleep, start school later'", Learning, Media and Technology, 40(2), (2015), 210-226.

(56) References Cited

OTHER PUBLICATIONS

Kripke, Daniel F., et al., "Short and Long Sleep and Sleeping Pills: Is Increased Mortality Associated?", Archives of General Psychiatry, 36(1), (Jan. 1979), 103-116.

Lim, Julian, et al., "A Meta-Analysis of the Impact of Short-Term Sleep Deprivation on Cognitive Variables", Psychological Bulletin, 136(3), (May 2010), 375-380.

Mark, Gloria, et al., "Neurotics Can't Focus: An in situ Study of Online Multitasking in the Workplace", Proceedings of CHI Conference on Human Factors in Computing Systems (CHI' 16), May 7-12, 2916, San Jose, CA, (May 7, 2016), 6 pgs.

Matchock, Robert L., et al., "Chronotype and time-of-day influences on the alerting, orienting, and executive components of attention", Experimental Brain Research, 192(2), (Feb. 2009), 10 pgs.

Monrose, Fabian, et al., "Authentication via Keystroke Dynamics", (c) 1997 ACM, Inc., CCS 97, Zurich, Switzerland, (1997), 48-56.

Murnane, Elizabeth L., et al., "Mobile Manifestations of Alertness: Connecting Biological Rhythms with Patterns of Smartphone App Use", Proceedings of 18th International Conference on Human-Computer Interaction with Mobile Devices and Services (MobileHCI '16), Sep. 6-9, 2016, Florence, Italy, (2016), 13 pgs.

Murnane, Elizabeth, et al., "Social (Media) Jet Lag: How Usage of Social Technology Can Modulate and Reflect Circadian Rhythms", Proceedings of ACM International Joint Conference on Pervasive and Ubiquitous Computing (UBICOMP '15), Sep. 7-11, 2015, Osaka, Japan, (Sep. 2015), 843-854.

Orne, Martin T., "On the Social Psychology of the Psychological Experiment: With Particular Reference to Demand Characteristics and their Implications", Journal of American Psychologist, 17(11), (Nov. 1962), 776-783.

Paparizzos, John, et al., "Screening for Pancreatic Adenocarcinoma Using Signals From Web Search Logs: Feasibility Study and Results", Journal of Oncology Practice, 12(8), (Aug. 2016), 737-744.

Purcell, Kristen, "Search and email still top the list of most popular online activities—Two acitivities nearly universal among adult internet users", Pew Internet & American Life Project. [Online]. Retrieved from the Internet: <URL: http://pewinternet.org/Reports/2011/Search-and-email.aspx, (Aug. 9, 2011), 1-15.

Roenneberg, Till, et al., "Comment: The human sleep project", Nature, 498(7455), (Jun. 2013), 427-428.

Ronneberg, Till, et al., "Life between Clocks: Daily Temporal Patterns of Human Chronotypes", Journal of Biological Rhythms, 18(1), (Feb. 2013), 80-90.

Sternberg, Daniel A., et al., "The largest human cognitive performance dataset reveals insights into the effects of lifestyle factors and aging", Frontiers in Human Neuroscience, vol. 7, Article 292, (Jun. 20, 2013), 1-10.

Van Dongen, Hans P. A., et al., "Circadian Rhythms in Fatigue, Alertness and Performance", In: Principles and Practice of Sleep Medicine (3rd Edition, W. B. Saunders, Philadelphia, PA), Kryger, M. H., et al., Editors, (2000), 1-31.

Vizer, Lisa M., et al., "Automated stress detection using keystroke and linguistic features: An exploratory study", International Journal of Human-Computer Studies, 67(10), (2009), 870-886.

Walch, Olivia J., et al., "A Global Quantification of "normal" Sleep Schedules using Smartphone Data", Journal of Science Advances, 2(5), (2016), 1-6.

West, Robert, et al., "From Cookies to Cooks: Insights on Dietary Patterns via Analysis of Web Usage Logs", Proceedings of 22nd International Conference on World Wide Web (WWW 10'3, May 13-17, 2013, Rio de Janeiro, Brazil, (2013), 1399-1409.

White, Ryen W., et al., "Early identification of adverse drug reactions from search log data", Journal of Biomedical Informatics, vol. 59, (Feb. 2016), 42-48.

Wright, Kenneth P., et al., "Circadian and wakefulness-sleep modulation of cognition in humans", Journal of Frontiers in Human Neuroscience, vol. 5, Article 50, (Apr. 2012), 1-12.

Bai, et al., "Will You Have a Good Sleep Tonight? Sleep Quality Prediction with Mobile Phone", In Proceedings of the 7th International Conference on Body Area Networks, Feb. 24, 2012, 7 Pages.

Exelmans, et al., "Sleep Quality is Negatively Related to Video Gaming Volume In Adults", In Journal of Sleep Research, vol. 24, Issue 2, Apr. 2015, pp. 189-196.

Laing, et al., "SleepExplorer", In Proceedings of Personal and Ubiquitous Computing, vol. 20, Issue 6, Nov. 1, 2016, pp. 985-1000.

"International Search Report and Written Opinion Issued in PCT Application No. PCT/US2018/034031", dated Nov. 26, 2018, 12 Pages.

Woods, et al., "Sleepyteens: Social Media Use in Adolescence is Associated with Poor Sleep Quality, Anxiety, Depression and Low Self-Esteem", In Journal of Adolescence, vol. 51, Aug. 1, 2016, pp. 41-49.

* cited by examiner

SLEEP MONITORING FROM IMPLICITLY COLLECTED COMPUTER INTERACTIONS

TECHNICAL FIELD

Embodiments described herein generally relate to inferring a user's sleep pattern and but without limitation, to inferring a user's physiological patterns based on collecting and comparing users implicitly collected computer interaction data.

BACKGROUND

Maintaining optimal cognitive performance is important relative to learning and productivity as well as avoiding industrial and motor vehicle accidents. Cognitive performance varies throughout the day thereby influencing the quality of performance, including how we use and interact with vehicles, devices, resources, and applications.

Cognitive performance decreases significantly after a loss of sleep. Understanding the real-world impact of sleep deficiency is critical. The estimated cost of fatigue to U.S. businesses exceeds $150 billion a year in absenteeism, workplace accidents, poor and delayed decision-making and other lost productivity on top of the increased health care costs and risk of disease. Despite the importance sleep-related performance, temporal variations of real-world performance based on sleep are not well understood and have never been characterized on a large scale.

Cognitive performance varies throughout each day and is driven in part by intrinsic, near 24-hour circadian rhythms. Existing research on the impact of sleep and circadian rhythms on cognitive performance has typically been restricted to small-scale laboratory-based studies that do not capture the variability of real-world conditions, such as environmental factors, motivation, and sleep patterns in real-world settings.

Daily patterns in human cognitive performance are typically modeled based on representations of three biological processes: (i) circulation rhythms (time-dependent, behavior-independent, near 24-hour oscillations); (ii) homeostatic sleep pressure (the longer awake, the more tired you become); and (iii) sleep inertia (performance impairment experienced immediately after waking up).

Existing sleep-related correlations are typically based on experimental studies in which participants are deprived of sleep and undertake regular, artificial tasks to measure performance instead of non-intrusively capturing performance through everyday tasks in real-world environments. In addition, the participants in an artificial laboratory setting can be influenced by their understanding of the study and subconsciously change their behavior.

Laboratory studies usually fail to account for a myriad of influences in the real-world, including motivation, mood, illness, environmental conditions, behavioral compensation including caffeine intake, and sleep patterns in the wild that are far more complicated than those enforced in research studies. In contrast, real-world cognitive performance varies throughout the day and is influenced by both circadian rhythms, chronotypes (morning/evening preference), and prior sleep duration and timing.

BRIEF DESCRIPTION OF THE DRAWINGS

In the drawings, which are not necessarily drawn to scale, like numerals may describe similar components in different views. Like numerals having different letter suffixes may represent different instances of similar components. Some embodiments are illustrated by way of example, and not limitation, in the figures of the accompanying drawings in which.

DETAILED DESCRIPTION

Figure 1:
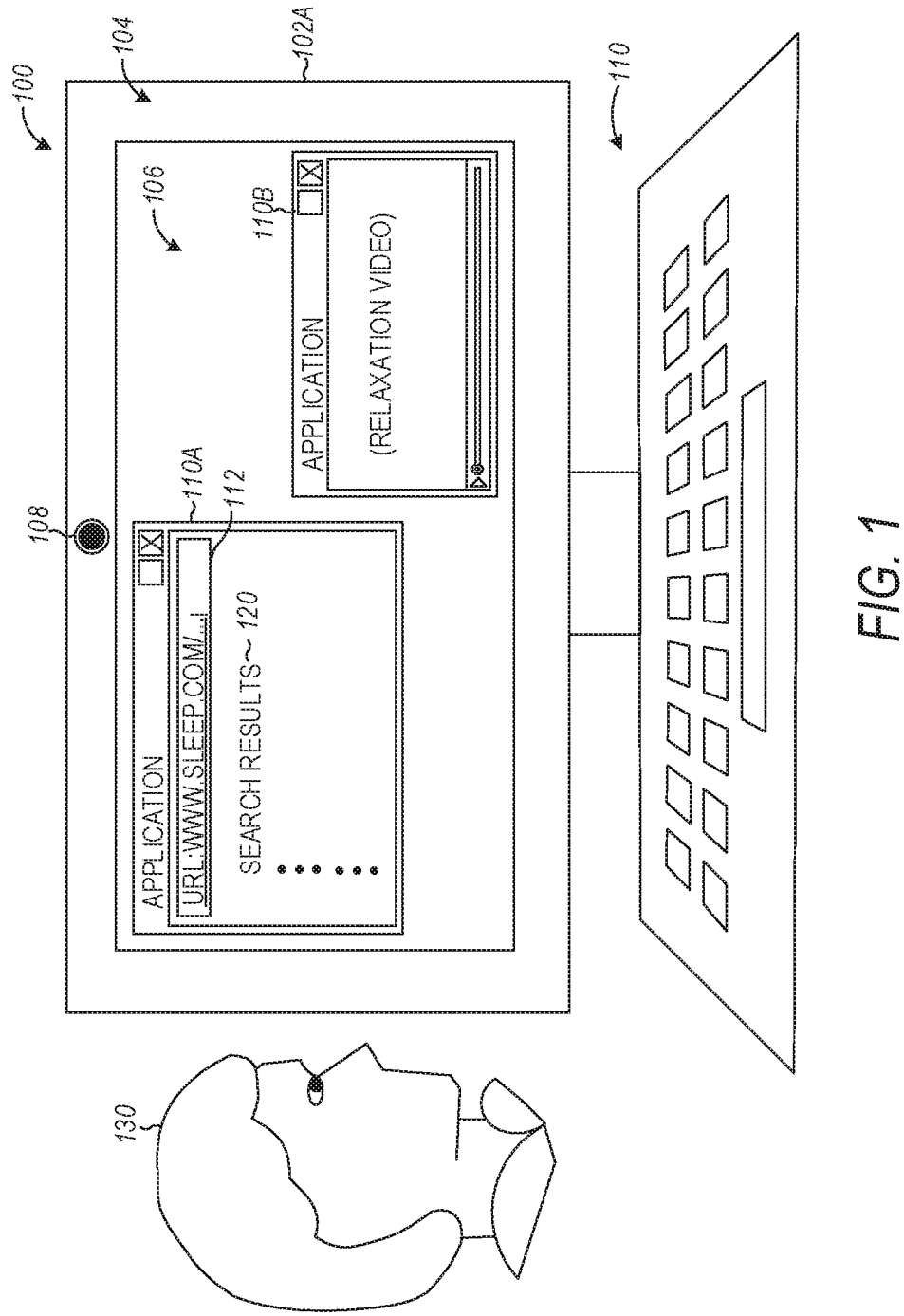
FIG. 1 illustrates an example system, in accordance with an example embodiment.

In some forms, cognitive performance may be measured based on a rate of individual keystrokes. In other forms, cognitive performance may be measured based on click interactions (e.g., on search results displayed by a web search engine). These implicitly (e.g., data collected through a user's general computing sessions without prompting the user to explicitly perform a function for testing purposes) collected computer interaction data may be correlated with sleep measures over time (e.g., by using a wearable sleep measuring device).

The methods, systems, machine-readable media, and devices described herein may take measurements of cognitive performance through everyday interactions with existing computing applications, e.g., speed of keystroke and click interactions on a web search engine, or other applications such as email, programming environments, bug report systems, and office suites. The measurements may be used to estimate factors affecting cognitive performance, e.g., sleep quality the night before or fatigue level at the current time, based only on logged action data.

Monitoring application usage by measuring implicitly collected computer interaction data may allow users to gain insights into performance and productivity that could be used to improve people's awareness of such patterns and to adapt the user experience accordingly (e.g., scheduling tasks intelligently in order to prevent or minimize human error, scheduling meetings based on participant's performance and chronotype profiles). As an example, the inferences that are generated may be tailored to individual users or user cohorts over time.

These inferences may be generated by comparing the implicit interaction data and with previously tracked sleep data in a sleep pattern correlation database. In some forms, the methods, systems, machine-readable media, and devices described herein may leverage tens of thousands of actual, non-implied, correlations between the current implicitly collected computer interaction data and sleep patterns (or other physiological traits) to make an inference about the user.

The systems may then offer suggestions based on that inference. One of the strengths of the inferences as compared to existing techniques is because the inferences are based on actual data instead of some form of modeling.

In some forms, the methods, systems, machine-readable media, and devices described herein may establish sleep pattern correlations to continuously and non-intrusively monitor human performance at population scale. The inferences and sleep pattern correlations that may be determined are relevant to (i) sleep scientists in pursuit of larger-scale real-world measurements of performance; and (ii) computer scientists who build tools and applications that may be affected by variations in human performance in order to address questions and challenges in the realm of public health.

Examples of other implicitly collected computer interaction data that may be correlated with sleep measures over time include mouse cursor activity (e.g., (i) speed of the mouse: (ii) number of times a user overshoots a link before they click; (iii) response time to system alerts and notifications; (iv) time to select items in standard UI elements like lists and dropdowns; and/or (v) scrolling characteristics such as speed.

A variety of different types of cursor movements may be part of the implicitly collected computer interaction data. Some examples include (i) cursor speed, (ii) cursor directness (i.e., the amount of deviation from shortest path), (iii) cursor, (iv) cursor acceleration, and/or (v) target overshooting with cursor (among other types of cursor movements).

There may also be meta-data associated with the various actions. Example meta-data may include the time the action occurs and the where the action occurs. In some forms, where the actions occur may serve to determine correlations based on a location of the user and sleep patterns.

In some forms, the users implicitly collected computer interaction data includes audible inputs and visual inputs that are obtained by the computer from the users. As an example, the audible inputs may include voice inputs that are generated by the user and detected by a computer. As another example, the visual inputs may include gaze inputs that are generated by the user and detected by a computer.

In other forms, the computer may obtain or image data of the user. The image data may be compared with previously collected image data to determine whether there is a change that signifies a change in sleep patterns (e.g., bags under the eyes of the user).

Another example of other implicitly collected computer interaction data that may be correlated with sleep measures over time include analyzing the content of search engine queries where users may be expressing fatigue. In other forms, the implicitly collected computer interaction data that may be correlated with sleep measures over time includes analyzing the content of social media postings where users may be expressing fatigue. Other forms of online computer interaction are contemplated to determine sleep pattern correlations.

In some forms, the methods, systems, machine-readable media, and devices described herein may measure (e.g., at the choice of a user) in a real-world setting (without any additional hardware or explicit testing) existing search engine interactions that occur billions of times per day. Human performance, as measured through implicitly collected computer interaction data, varies throughout the day based on chrono-type and sleep.

The inferences that are based on the sleep pattern (or other physiological aspect) correlations may provide insight about sleep and performance due to the power of harnessing online activities to study human cognition, motor skills, and public health. The large-scale biometric sensing from online data that encompasses implicitly collected computer interaction data enables (i) studies of sleep and performance outside of small laboratory settings without actively inducing sleep deprivation; (ii) non-intrusive measurement of cognitive performance without forcing individuals to interrupt their work or to perform separate artificial tasks; and/or (iii) the identification of realistic measures of real-world cognitive performance based on frequent tasks and interactions or continuous monitoring of measurements.

As examples, inferences and sleep pattern correlations may be obtained from computing applications such as email, programming environments, bug report systems, office suites, and others. The inferences and sleep pattern correlations may provide insights on performance and productivity that are gained by monitoring these applications to possibly improve a user's awareness of patterns and/or to adapt the user experience appropriately. As an example, tasks may be scheduled intelligently in order to prevent or minimize human error based on participant's performance and chronotype profiles.

FIG. 1 illustrates a schematic diagram of an example implicit computer interaction data collection system 100, according to various example embodiments. As shown, the system 100 includes device 102A. Device 102A can be a laptop computer, a desktop computer, a terminal, a mobile phone, a tablet computer, a smart watch, a personal digital assistant (PDA), a wearable device, a digital music player, a server, and the like. User 130 can be a human user who may interact with device 102A, such as by providing various inputs (e.g., via an input device/interface such as a keyboard, mouse, touchscreen, etc.).

In certain implementations, device 102A can include or otherwise be connected to various components such as display device 104 and one or more tracking component(s) 108. Display device 104 can be, for example, a light emitting diode (LED) display, a liquid crystal display (LCD) display, a touchscreen display, and/or any other such device capable of displaying, depicting, or otherwise presenting user interface 106 (e.g., a graphical user interface (GUI)).

Tracking component(s) 108 can be, for example, a sensor (e.g., an optical sensor), a camera (e.g., a two-dimensional or three-dimensional camera), and/or any other such device capable of tracking implicitly collected computer interaction data, as described herein. It should be understood that while FIG. 1 depicts display device 104 and tracking component(s) 108 as being integrated within a single device 102A (such as in the case of a laptop computer with an integrated webcam or a tablet/smartphone device with an integrated front-facing camera), in other implementations display device 104 and tracking component(s) 108 can be separate elements (e.g., when using a peripheral webcam device).

For example, as shown in FIG. 1, device 102A can present user interface 106 to user 130 via display device 104. User interface 106 can be a graphical depiction of various applications executing on device 102A (and/or any other such content displayed or depicted via display device 104), such as application 110A (which can be, for example, a web browser) and application 110B (which can be, for example, a media/video player).

Such application(s) can also include or otherwise reflect various content elements (e.g., content elements search results 120). Such content elements can be, for example, alphanumeric characters or strings, words, text, images, media (e.g., video), and/or any other such electronic or digital content that can be displayed, depicted, or otherwise presented via device 102A.

Various applications can also depict, reflect, or otherwise be associated with a content location 112. Content location 112 can include or otherwise reflect a local and/or network/remote location where various content elements can be stored or located (e.g., a Uniform Resource Locator (URL), local or remote/network file location/path, etc.).

It should be noted that while FIG. 1 (as well as various other examples and illustrations provided herein) depicts device 102A as being a laptop or desktop computing device, this is simply for the sake of clarity and brevity. Accordingly, in other implementations device 102A can be various other types of devices, including but not limited to various wearable devices.

For example, in certain implementations device 102A can be a virtual reality (VR) and/or augmented reality (AR) headset. Such a headset can be configured to be worn on, or positioned near, the head, face, or eyes of a user. Content such as immersive visual content (that spans most, or all, of the field of view of the user) can be presented to the user via the headset. Accordingly, such a VR/AR headset can include or incorporate components that correspond to those depicted in FIG. 1 and/or described herein.

By way of illustration, a VR headset can include a display device, e.g., one or more screens, displays, etc., included/incorporated within the headset. Such screens, displays, etc., can be configured to present/project a VR user interface to the user wearing the headset. Additionally, the displayed VR user interface can further include visual/graphical depictions of various applications (e.g., VR applications) executing on the headset (or on another computing device connected to or in communication with the headset).

Additionally, in certain implementations such a headset can include or incorporate tracking component(s) such as are described/referenced herein. For example, a VR headset can include sensor(s), camera(s), and/or any other such component(s) capable of detecting motion or otherwise tracking the eyes of user (e.g., while wearing or utilizing the headset). Accordingly, the various examples and illustrations provided herein (e.g., with respect to the device 102A) should be understood to be non-limiting as the described technologies can also be implemented in other settings, contexts, etc. (e.g., with respect to a VR/AR headset).

Figure 2:
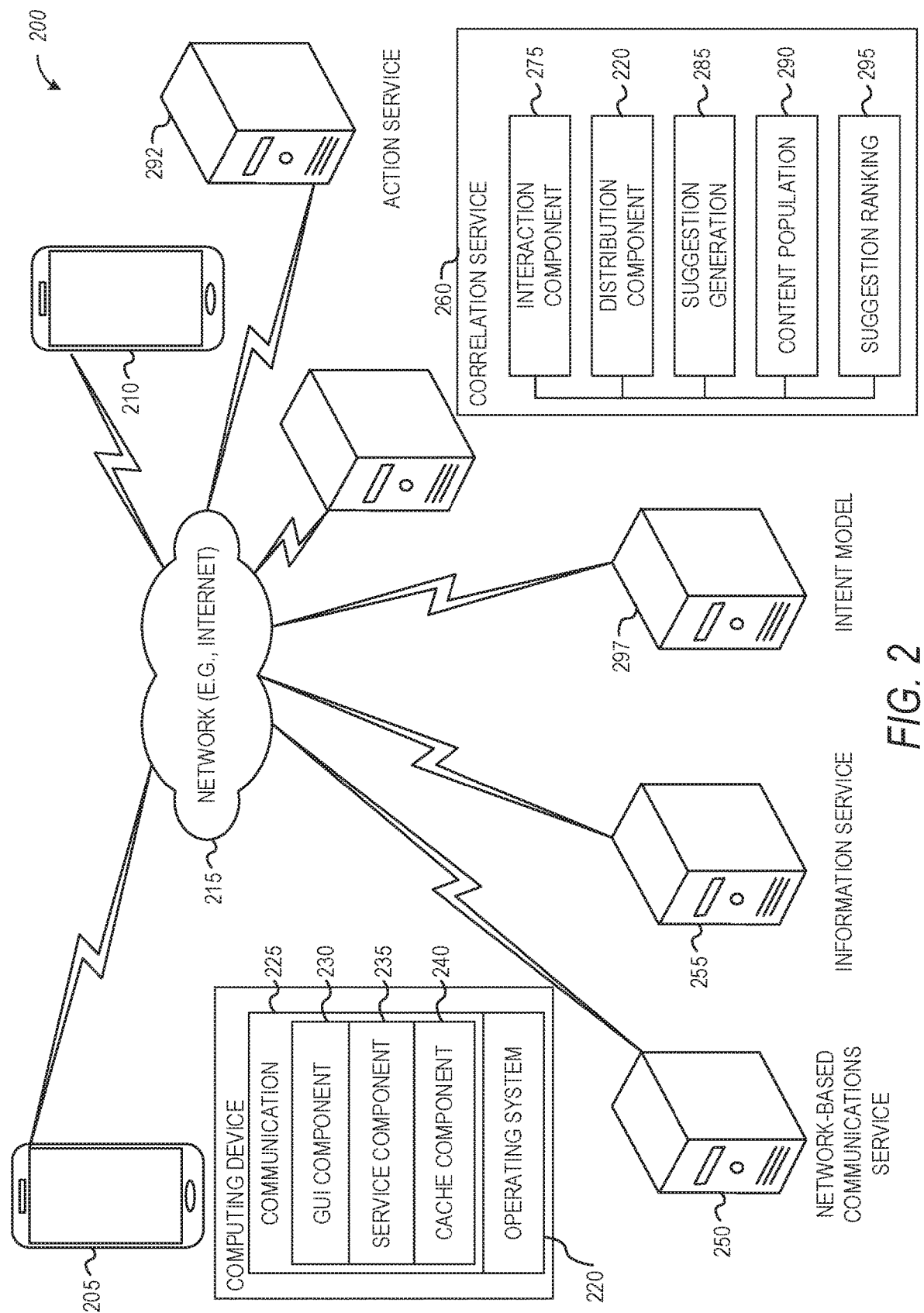
FIG. 2 shows a system diagram of a network-based communications system for generating an inference according to some examples of the present disclosure.

Turning now to FIG. 2, a system diagram of the network-based communications system 200 showing further aspects the implicit computer interaction data collection system 100. The components of FIG. 2 may be configured to communicate with each other, for example, via a network coupling (such as network 215), shared memory, a bus, a switch, and the like.

In various examples, the servers and components shown in FIG. 2 may communicate via one or more networks (not shown). The networks may include local-area networks (LAN), wide-area networks (WAN), wireless networks (e.g., 802.11 or cellular network), the Public Switched Telephone Network (PSTN) network, ad hoc networks, cellular, personal area networks or peer-to-peer (e.g., Bluetooth®, Wi-Fi Direct), or other combinations or permutations of network protocols and network types. The networks may include a single local area network (LAN) or wide-area network (WAN), or combinations of LAN's or WAN's, such as the Internet.

It will be appreciated that each component may be implemented as a single component, combined into other components, or further subdivided into multiple components. Any one or more of the components described herein may be implemented using hardware (e.g., a processor of a machine) or a combination of hardware and software (for example machine 100 of FIG. 1). For example, while the figure shows the network-based communications service 250, information service 255, correlation service 260, action service 292, and inference models 297 as separate computing devices in communication with each other through network 215, the functionality of those components may be implemented by the same computing device, or by different computing devices connected through a different network (e.g., a local area network LAN) than network 215.

Computing devices 205 and 210 (shown as mobile devices such as smart phones) may include an instance of an operating system 220 and a communication application 225. Operating system 220 may provide one or more services to applications, such as a communication application 225. Services may include memory management, scheduling, multi-tasking, notifications, interrupts, event notifications, hardware interfaces, and the like. Communication application 225 may be a network-based communication application and may include a GUI component 230, service component 235, and cache component 240. GUI component 230 may render one or more GUIs.

Service component 235 may connect to the network-based communications service 250 and may send messages entered by the user of the computing device 205 via the GUI provided by the GUI component 230 to one or more other users of the network-based communications service 250. Service component 235 may receive one or more other messages from other users through the network-based communications service 250 and may cause those communications to be displayed in the GUI provided by the GUI component 230.

Service component 235 may also receive receiving implicitly collected computer interaction data of a user from a computing device (e.g., from one of the devices 102A, 205, 210). The service component 235 may also access a data store of implicitly collected computer interaction data, the implicitly collected computer interaction data being correlated with sleep patterns of users.

It should be noted that the implicitly collected computer interaction data may be collected from any number of sources and may be standardized and/or harmonized. Accordingly, once a data store (e.g., file system, relational database, NoSQL database, flat file database) is populated with enough semantically intact data, the data may be mined, stored, queried, audited, and validated. The implicitly collected computer interaction data may originate from a number of forms such as unstructured data, a spreadsheet, a relational database, Extensible Markup Language (XML), JavaScript Object Notation, etc. In some instances, a service (e.g., a web service) may map or translate the various formats into a common format for easier data mining.

The correlation service 260 may compare the users implicitly collected computer interaction data to the previously collected computer interaction data, and infer the user's sleep pattern based on the comparing. As an example, the correlation service 260 may compare a specific user's data (e.g., wake up time) with previously collected and correlated sleep data for a population of other users in order to determine an inference regarding the specific user's data.

In some forms, the implicitly collected computer interaction data includes keyboard inputs. As an example, the client device 100 may include a touch screen and the users implicitly collected computer interaction data includes the user's contacts with a touch screen.

The correlation service 260 may also cause the sleep inferences to be displayed via the GUI provided by the GUI component 230. Additionally, user input (i.e., feedback) on an inference may be sent by the service component 235 to the correlation service 260.

Based on the feedback from one or more user's, the correlation service 260 may take an action on behalf of the user, send additional content or information (that may have been requested by the user), and to customize inferences for the user. As a result, additional information, content, or implicitly collected computer interaction data may be sent or received by the correlation service 260.

The service component 235 may cause this additional information to be displayed in a GUI provided by GUI component 230. In other examples, information needed for the interactions are sent by the correlation service 260 along with the inference. The inference may comprise the inference that is initially displayed (e.g., "PRIMARY SLEEP BENEFITS ARE DERIVED WHEN SLEEPING FROM 9 PM TO 5 AM"), and when selected, additional information (e.g., "RELAXATION TECHNIQUES FOR SLEEPING") that is sent by the correlation service 260 may then be displayed.

Cache component 240 may cache the communications and the suggestions and allow users to review the past communications and past inferences. Users may select or activate the past inferences at any time while their communication session is active. In some examples, the cache component may allow for reviewing past communications and inferences and activating those inferences at any time.

Network-based communications service 250 may receive communications (which may include implicitly collected computer interaction data) from computing devices and route those communications to other computing devices participating in the network-based communication session. For example, a communication from computing device 205 may be routed to computing device 210 if computing device 210 and computing device 205 are in a communications session together. Additionally, network-based communications service 250 may route a copy of these communications to correlation service 260. Suggestions from correlation service 260 may be routed directly to participants in the communication session, or through the network-based communications service 250.

Correlation service 260 may receive communications from service component 235 or from the network-based communications service 250 and may generate one or more inferences and return those inferences to the computing devices in the communication session. These inferences may be personalized for each user (or group of users) and thus, inferences given to computing device 205 may be different than inferences given to computing device 210 given the same communication messages. Inferences may be personalized based upon a user profile stored at the computing device or a network-based profile service (e.g., a network based computing device storing a plurality of user profiles to provide for inter-computing device knowledge of the profiles). Some example methods to infer sleep patterns are summarized in the next series of paragraphs. Additional implementations are discussed further herein.

In some example forms, inferring the user's sleep pattern based on comparing the implicitly collected computer interaction data includes inferring based on the time between successive keyboard inputs. As an example, the inferring of the user's sleep pattern based on the comparing may include inferring based on an average time between successive keyboard inputs for at least three keyboard inputs. In other examples, the inferring may be based on any of a max, median, mode, etc., time between successive keyboard inputs (or any combination of time-based factors).

In some implementations, the user's computer implicit interaction data includes cursor operations on a display of the computing device. As an example, the user's cursor operations may provide an input that relates to an amount of time it takes to select a newly presented object on the display by using the cursor (or using a touch screen in other forms.

In some forms, the newly presented object may be part of a plurality of newly presented objects on the display. Therefore, the amount of time it takes to select the new object from among the plurality of objects may provide a strong correlation relating to sleep patterns.

In addition, inferring the user's sleep pattern based on the comparing may include inferring based on a position of the newly presented object within the plurality of newly presented objects. As an example, the distance from a current selection to the preceding selection to select the new object from among the plurality of objects may provide be an additional factor demonstrating a strong correlation relating to sleep patterns.

Correlation service 260 may include a distribution component 280. Distribution component 280 may distribute the communications received from the network-based communications service 250 to one or more inference models, such as inference model 297. The inference model 297 may determine inferences based upon rules—e.g., heuristics such as determining inference based upon the presence of one or more particular keywords. In other examples, the inference model 297 may be an unsupervised or supervised machine-learning model. Examples include natural language processing, decision trees, random forests, support vector machines, and the like.

Inferences may be developed that operationalize a large body of sleep and cognitive performance data. The inferences may demonstrate the relative effects of circadian rhythms, homeostatic sleep drive, and sleep inertia align with expectations from laboratory-based sleep studies. As an example, the impact of insufficient sleep (e.g., two consecutive nights with less than six hours of sleep) may be associated with decreases in cognitive performance, which may last for a period of days.

As an example, the computing system may propose that a person sleeps more (or less) in a given night, and then measures their attention in the following day (e.g., by events related to the use of a computer). An example causal link that exists, which form the basis of a sleep pattern correlation, is that shortening the sleep should reduce attention. Once a correlation is found, a probability is computed that may serve to determine a numerical representation of the correlation value that represents the known correlation and its strength.

In some examples, the implicitly collected computer interaction data may be sent to multiple inference models, each of which is designed to determine a different inference or a different type of inference. In some examples the implicitly collected computer interaction data may be sent to multiple inference models, each of which is a different type of model; that is, one model might be rule based, another might be a machine-learning model.

Inference models 297 may respond with one or more calculated inferences. Each inference model 297 may be trained and/or designed to detect certain types of inferences. For example, one model may be trained for a first type of inference and a second model may be trained for a second type of inference. For example, one model may be designed to detect inferences relating to sleep patterns and implicitly collected computer interaction data.

Another model may be designed to detect inferences relating sleep and physical activity. Other examples include information about diet, stress, physical ailments and/or travel. By providing the communication to a number of specially trained models looking for specific inferences, the system can more accurately determine inferences for users than providing the communication to a general model.

In some examples, inference models 297 may not respond if the communication does not produce an inference that is above a certainty threshold. However, multiple models may respond with a calculated inference. Suggestion generation component 285 may then generate suggestions for each inference based on one or more sleep pattern correlations returned by the models.

The inferences may generate suggestions that may be categorized as actions (e.g., recommended sleep times and/or duration), content suggestions (providing information about relaxation and exercise) and the like. Example action suggestions include using a particular application, going to a website, setting a reminder (e.g., to take a break), and the like. Example content suggestions may include providing information on diet, sleep, relaxation and/or stress (e.g., by showing a document, showing a video, showing an audio clip, showing a picture, and the like).

Inferences may be based upon one or more if-then-else rule sets that generate suggestions to try to improve the effects of sleep based upon the returned inferences. For example, if the returned inference is that the user is sleeping too much, then the suggestion may be to provide more information on the effects of over sleeping. As another example, if the returned inference is that the user wishes to get up at a certain time every day, then the suggestion may be a calendar reminder about bedtime. Other methods of converting the inferences to suggestions that may improve sleep may be utilized, such as decision trees, random forests, and the like.

Content population component 290 may populate the suggestions with content from one or more sources, such as information service 255 (e.g., a calendar service, a search engine, a website, or other database). Content population component 290 may also utilize one or more Application Programming Interfaces (API)s to communicate with these services.

The content population component may utilize a user profile of the user. Known preferences of the user in the user profile may be utilized to populate content. For example, a user's bedtime preferences may be utilized to select a sleep schedule. This allows the suggestions to be personalized to the user's likes and dislikes. For example, the system may learn that the user is a vegetarian, and may suggest vegetarian diets that promote sleep.

Suggestion ranking component 295 may rank the inferences that were determined by suggestion generation component 285. Suggestion ranking component 295 may have rules that specify rankings. In some forms, a variety of different heuristics may be utilized to the rank the suggestions within the suggestion generation components. As an example, the heuristics may consider the actual subject of the inference. For example, calendar action inferences may be ahead of sleep schedule inferences and so on.

In some examples, the heuristics may be adjusted based upon feedback from all users of the correlation service 260. For example, if users typically interact with (e.g., select) action suggestions generated by the inferences more than the content suggestions generated by the inferences, the action suggestions may be prioritized over the content suggestions. Thus, by using feedback, a global user model may adjust the heuristics to better meet user needs.

In some examples, in addition to a global user model, each user may have a learned preference for certain types of suggestions generated by the inferences. Thus, even though the global model may determine that the larger population of users interact with the action suggestions more than the content suggestions, if a particular user likes content suggestions based on the inferences more than action suggestions based on the inferences, content suggestions may be prioritized over other suggestion types. Example models may include neural networks, decision trees, random forests, regression algorithms, and the like. The example models may be (i) individual user models; (ii) cohort models; and/or (iii) global models.

In some examples, the three models (heuristic model, global model, individual model) may be combined such that the models may have a hierarchy. Thus, the individual model may control, unless there is insufficient personal interaction data, in which case the global model will control, unless there is insufficient global interaction data, in which case heuristics are utilized.

In other examples, each model may contribute to the final ranking. For example, each model may assign a fixed amount of points to each suggestion per the rules of the model. Each suggestion based on the inference(s) may then be scored by using a weighted summation combining the point values for each suggestion and/or inference according to each model. Each model may be weighted according to a perceived accuracy of the model to the user's preferences. For example, the individual model may be weighted greater than the global model, and both may be weighted higher than the heuristic model. Weights may change dynamically over time based upon user feedback in the form of explicit feedback—e.g., a GUI element indicating satisfaction or dissatisfaction with a suggestion or based upon implicit feedback in the form of interactions with suggestions based on some inferences (interaction with a suggestion signifying satisfaction).

Rankings may be calculated based upon the type of inference and/or suggestion (action vs. content), but also may be ranked based upon the actual suggestion content. For example, if the inference is determined to be more sleep is better for cognition, suggestions may be (i) go to bed earlier; (ii) sleep longer and/or (iii) sleep later. All three are action suggestions, but these suggestions may be ranked based upon the preferences of a user for these specific actions.

Interaction component 275 handles user interactions with suggestions by exchanging information (such as content determined by the content population component 290), with users in order to carry out an action suggestion, and the like. Action services 292 may be calendar services, exercise services, diet services, relaxation services and other action services.

Figure 3:
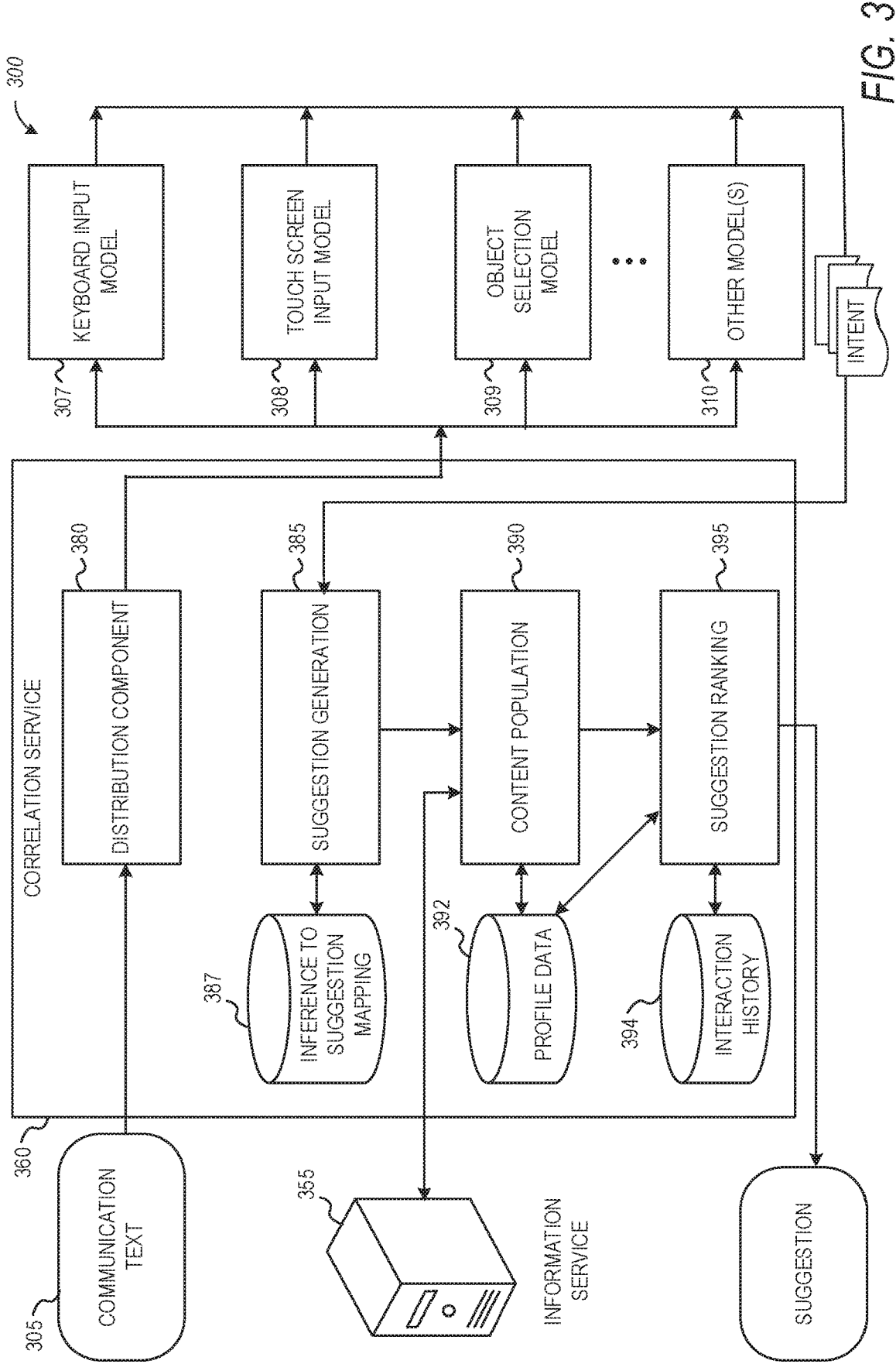
FIG. 3 shows a data flow of generating an inference according to some examples of the present disclosure.

Turning now to FIG. 3, a data flow of an inference generation 300 is shown according to some examples of the present disclosure. Correlation service 360 may be an example of correlation service 260. In some examples, distribution component 380 may be an example of distribution component 280. In some examples, suggestion generation component 385 may be an example of suggestion generation component 285. In some examples, content population component 390 may be an example of content population component 290. In some examples, suggestion ranking component 295 may be an example of suggestion ranking component 295.

As noted above with respect to FIG. 2, all, or some, of the components are configured to communicate with each other, for example, via a network coupling, shared memory, a bus, a switch, and the like. It will be appreciated that each component may be implemented as a single component, combined into other components, or further subdivided into multiple components. Any one or more of the components described herein may be implemented using hardware (e.g., a processor of a machine) or a combination of hardware and software.

Communication text 305 (which may include all types of implicitly collected computer interaction data that is generated when a user interacts with a computing device) from a communication session is handled by the distribution component 380. Distribution component 380 inputs the communication text (or other type of input) 305 to one or more inference models 307-310.

As an example, keyboard input model 307 (which may identify implicitly collected computer interaction data referenced within the communication text 305) may determine inferences that are based on sleep pattern correlations referenced in the communication text 305 (e.g., by receiving data related to the speed of keystrokes). Touch screen input model 308 may determine from the communication text 305 whether (and how) the user interacted with a touchscreen, or the like (e.g., by receiving data related to the speed of contacts with a touch screen). Object interaction model 309 may determine from the communication text 305 whether (and how) the user interacted with a mouse to select an object on the display, or the like (e.g., by receiving data related to the speed in which a user selects an object found in a search result from the search engine of a web browser).

As noted in FIG. 3, any number of other models may be utilized to determine intent, such as object model 310. The models 307-310 may be implemented as part of correlation service 360, or may be separate services in communication with the correlation service 360. As previously noted, the models may be machine-learning models, including supervised or unsupervised learning models. Examples include neural networks, regression, natural language processing, random forest, decision tree, decision jungle, or other models.

Models may interact with action services, such as action service 292 of FIG. 2 to further determine one or more properties of the user in order to better determine an inference. For example, the action service 292 may be a calendar service (e.g., MICROSOFT OUTLOOK®) that may keep track of a user's appointments and meetings. The models may consult the calendar service to determine if a particular suggestion based on an inference is compatible with properties of the user (e.g., the user's schedule). For example, if the user has a meeting at 7 AM, then a suggestion that causes the user to sleep no later than 6 AM may be optimal.

The suggestion generation component 385 receives the determined inferences and maps them to suggestions. Returned inferences may include content as well as, or instead of, semantic meanings, such as text inputs via a keypad and the like. For example, the suggestion generation component 385 uses a database, such as an inference to suggestion mapping 387, which may contain possible inferences and an indication of the corresponding sleep-related suggestion. For example, a sleep time suggestion may have a corresponding calendar entry suggestion.

In other examples, rather than a table, the inference to suggestion mapping 387 may be rule based, with if-then statements that are evaluated against the value of the inference to determine the suggestion. For example, if the inference is to create a calendar entry, then the corresponding suggestion is to create a calendar entry. More than one suggestion may be created from a single inference.

Suggestion generation component 385 may interact with action services, such as action service 292 of FIG. 2 to determine one or more properties of the user. For example, the action service may be a calendar service (e.g., MICROSOFT OUTLOOK®) that may keep track of a user's appointments and meetings. The suggestion generation component 385 may consult the calendar service to determine if the suggestion is compatible with properties (e.g., the user's preferred sleep schedule) of the user. For example, if the user is already busy, then a suggestion that the user needs to sleep at another time might make a better suggestion.

Content population component 390 may take the suggestions and populate content in the suggestions. For example, by contacting an information service 355. Content population may also utilize profile data 392 of the user. Profile data 392 may be obtained based upon previous usage of the suggestion service 360 and may include action preferences, content preferences, location information, and the like. For example, the profile data 392 may include a user's sleep preferences, diet preferences, exercise preferences, and the like.

The profile data 392 may be context specific, such that it stores preferences for varying contexts of the user (or similar groups of users). For example, it may store that the user prefers to sleep late on weekends, but does not like to sleep past 7 AM on weekdays. The system may then populate suggestions for weekdays, but other suggestions for weekends.

Suggestion ranking component 395 may rank the suggestions and select one or more of the suggestions to send to the computing device of the user. As noted, the suggestion ranking component 395 may consult both user profile data 392 and interaction history 394 to rank the inferences and/or suggestions relative to each other based upon a global model that is built using interactions of all users with all inferences and/or suggestions for all implicitly collected computer interaction data analyzed by the suggestion service 360, as well as an individual model that is built using interactions of the current user with the inferences and/or suggestions for all implicitly collected computer interaction data for that user.

The suggestion-ranking component 395 may suggest all suggestions relative to an inference or may select a subset of suggestions relative to an inference to send to the user's computing device based upon the ranking. For example, the suggestion-ranking component 395 may select a top predetermined number or percentage of high ranking suggestions (e.g., top three, or top 10%) and send them to the computing device of the user. In other examples, the suggestion-ranking component 395 may determine a screen size of the user's computing device.

The suggestion-ranking component 395 may select a set of suggestions to send to the user's computing device that maximizes a total utility of suggestions considering constraints on the length of the suggestions and a size of the suggestion area of a GUI of the computing device of the user. For example, a ranking may be reflected in a number of points where a higher ranking means higher point values.

In some examples, the suggestions selected by the suggestion-ranking component 395 may comprise different types of suggestions. For example, a content suggestion and an action suggestion. As previously noted, the system may record interactions with the given suggestions and the system may use this feedback to learn how to better rank the suggestions. In some examples, this feedback may be shared with the inference model 297 to allow the inference model to better learn the appropriate inference. Thus, a user's interaction with a particular suggestion provides both an indication as to how inferences and corresponding suggestions should be ranked, and provides an indication as to whether the implicitly collected computer interaction data determined by the inference models correctly identified the inference of the implicitly collected computer interaction data. Lack of interaction with suggestions also indicates that those suggestions may be deprioritized and that the inference model was incorrect in its determination of the implicitly collected computer interaction data.

Figure 4:
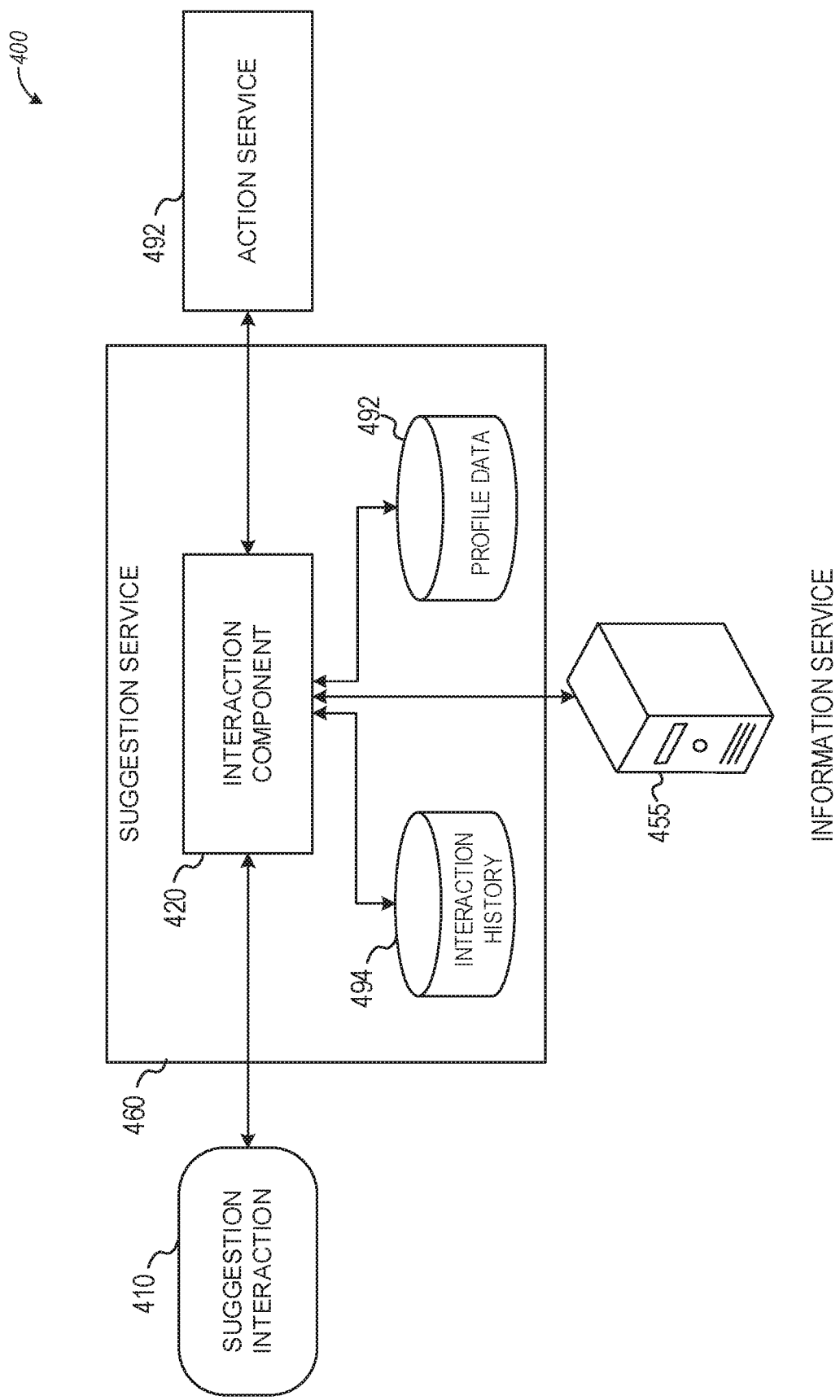
FIG. 4 shows a data flow of generating an inference according to some examples of the present disclosure.

Turning now to FIG. 4, a data flow of a suggestion generation 400 is shown according to some examples of the present disclosure. Suggestion service 460 may be an example of suggestion service 360 and 260 according to some examples of the present disclosure. An interaction with a suggestion 410 is received at the suggestion service 460 by the interaction component 420.

Interaction component 420 may respond with additional information regarding the suggestion or additional context. For example, preferred wake-up times of the user, additional context, and the like. In some examples, this additional information may be obtained from an information service 455 (which may be an example of information service 355, 255). The user may interact with this additional content, such as by selecting wake-up time for weekdays and receiving more content about the user's calendar. This ensures a premium user experience without the user having to leave the user interface of the application preferred by the user.

The interactions and the additional content may be created with the help of the profile data 492 and interaction history 494. Profile data 492 may be an example of profile data 392 of FIG. 3. Interaction history 494 may be an example of interaction history 394 of FIG. 3. Upon interacting with a suggestion, the interaction component 420 may update the interaction history 494 so that the suggestion-ranking component may update its user-based model.

Interaction component 420 may interact with an action service 491. Action service 491 may be an example of action service 292 of FIG. 2. Interaction component 420 may consult with action service 491 to provide content and interactions associated with the inferences and/or suggestions (e.g., sleep schedules, exercise schedules, diet recommendations and the like). Interaction component 420 may also interface with action service 491 to implement any action suggestions selected by the user. For example, selecting medications, foods to eat, vitamins to take, or the like.

Figure 5:
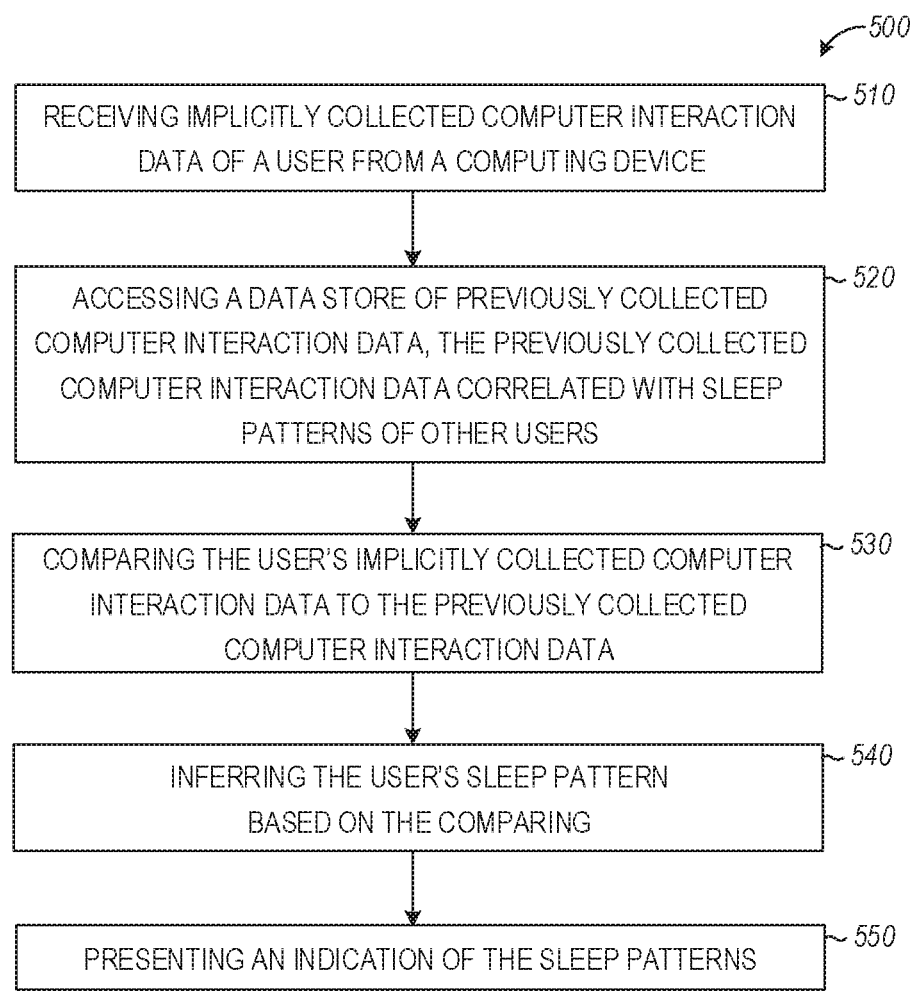
FIG. 5 is a flow chart illustrating an example method of comparing users implicitly collected computer interaction data to the previously collected computer interaction data to infer a user's sleep pattern, in accordance with some embodiments.

FIG. 5 illustrates a flowchart of method 500 of forming inferences by comparing implicitly collected computer interaction data. The method 500 may be implemented at a computing system, such as any of the devices or components described herein.

At operation 510, the methods, systems, machine-readable media, and devices receive one or more types of implicitly collected computer interaction data of a user from a computing device (e.g., computing device 110 of FIG. 1). In some forms, the implicitly collected computer interaction data includes keyboard inputs. As another example, the client device 100 may include a touch screen and the users implicitly collected computer interaction data includes the user's contacts with a touch screen.

There are a variety of different types of user's contacts with a touch screen that could be collected as part of the implicitly collected computer interaction data. Some examples include swipe, pan and zoom movements (among others) on the touch screen.

At operation 520, the methods, systems, machine-readable media, and devices described herein access a data store of previously collected computer interaction data. The previously obtained implicitly collected computer interaction data is correlated with sleep patterns of users (e.g., by using correlation services 260, 360, 460). The previously collected implicitly collected computer interaction data and corresponding sleep pattern correlations may be accessed from a database (e.g., information service 255 or suggestion service 260 in FIG. 2) located in any of the components described herein.

Accessing the correlation may identify a type (e.g., biometric, typing speed) of correlation. The sleep pattern correlations may be generated using any correlation technique, for example, regression (e.g., linear regression, power regression, logarithmic regression, exponential regression, etc.) may be used. These correlations may be stored in the same database as the implicitly collected computer interaction data or stored in different databases.

In some aspects of the subject technology, the methods, systems, machine-readable media, and devices include an input/output component (e.g., computing device 100 in FIG. 1 or a mobile phone, a tablet computer, a laptop computer, a desktop computer, a server, and the like) that receives implicitly collected computer interaction data. The implicitly collected computer interaction data may be received in the form of one or more events (e.g., sleeping running, typing, eating) and/or metadata about the events (e.g., metadata that indicates keystroke measurement, cursor movement, heart rate, distance run, time spent running, calories burned, and the like). The events and their metadata may be manually entered by the user or automatically received from computing devices 102A, 205, 210, a sensor or some other data-collecting device (e.g., a fitness tracker).

In some forms, the computing system 100 retrieves (and possibly stores) the correlations from another computing device (i.e., a separate database on another computing device). In some implementations, the events may be generated (or triggered) by the computing system, a user of the computing system or in other ways. Example computer system types of events include, but are not limited to, a button being clicked, a mouse moving, text entry (e.g., typing speed and accuracy), a programming closing, a scrollbar being adjusted (e.g., speed and accuracy of adjustment), scroll wheel movement (e.g., speed and accuracy of movement), and the like.

The computing system may access events that indicate implicitly collected computer interaction data is available from multiple different sources. The computing system may access information about events (and the corresponding implicitly collected computer interaction data) of the user and possibly of other similar users.

According to some examples, events are objects in the programming language Java or another programming language. They may come from a series of classes stored in java.util.EventObject (or another series of classes or different programming language structure).

In some forms, the implicitly collected computer interaction data may be stored with an indication of their corresponding sleep pattern correlation strength (for example in the form of a correlation coefficient as also referred to herein as a correlation value). The sleep pattern correlation values may be generated for individuals, groups of individuals that are similar to the user, or an entire population of users from databases containing various types of implicitly collected computer interaction data.

As an example, the sleep pattern correlation values may be in the form of a severity score based on the difference between the amount of sleep inferred and the recommended quantity of the sleep (e.g., given user demographics or some other factor). The severity score may determine (i) the selection of a suggested action (ii) the content of the suggested content, and/or (iii) the wording of the suggestion (among other information types of information that may be included in a suggestion).

At operation 530, the methods, systems, machine-readable media, and devices described herein compare the users implicitly collected computer interaction data to the previously collected computer interaction data (e.g., by using correlation service 860 in FIG. 2). The comparison may be generated because of a communication between users of a network-based communication service. The communication may have been received by the user from another user or sent by the user to another user.

In some implementations, the user's computer implicit interaction data includes one, some or all cursor operations on a display of the computing device. As an example, the user's cursor operations may provide an input that relates to an amount of time it takes to select a newly presented object on the display by using the cursor.

In some forms, the newly presented object may be part of a plurality of newly presented objects on the display. Therefore, the amount of time it takes to select the new object from among the plurality of objects may provide a strong correlation relating to sleep patterns.

In addition, inferring the user's sleep pattern based on the comparing may include inferring based on a position of the newly presented object within the plurality of newly presented objects. As an example, the distance from a current selection to the preceding selection to select the new object from among the plurality of objects may provide be an additional factor demonstrating a strong correlation relating to sleep patterns.

The communication may be submitted to different models that analyze the sleep pattern correlations. Each of the models (as described with reference to FIGS. 2-4) that analyzes the correlations may be executed on one or more computing devices.

The comparison may be based upon the events associated with the user, a population of users that are similar to the user, or an entire population of users. Each user may therefore have their own different personalized sleep pattern correlations. The correlation values with respect to a particular user may be learned over time from interactions with the network-based communication service and other applications on one or more computing systems of the user.

The sleep pattern correlations may be ranked in order of the perceived strength (e.g., correlation coefficients closer to 1 or −1 are strongly than correlation coefficients of 0) of the correlation. Utilizing a number of different models to determine sleep pattern correlations may be more accurate than general models that attempt to discern general correlations.

At operation 540, the methods, systems, machine-readable media, and devices described herein infer the user's sleep pattern based on the comparing. As an example, the user's sleep pattern may be inferred by using inference model 297 (as shown in FIG. 2). In some forms, inferring the user's sleep pattern includes inferring based on the time between successive keyboard inputs. As an example, the inferring of the user's sleep pattern may include inferring based on an average time between successive keyboard inputs for at least three keyboard inputs.

In some examples, a machine learning classification algorithm such as a multiclass logistic regression algorithm, a multiclass neural network, a multiclass decision forest, or the like may learn appropriate inferences based on the sleep pattern correlations. The machine-learning algorithm may utilize training data in order to identify appropriate inferences based upon the learned relationships between the implicitly collected computer interaction data and sleep pattern correlations.

In some forms, heuristic models may set up a priority ordering based upon the type of inference. The inference models may modify these rules based upon user interactions and types of implicitly collected computer interaction data. In other examples, other machine learning models may be utilized such as logistic regression, linear regression, neural networks, decision trees, decision forests, and the like. These models may be initially trained using the heuristic model, then the model may be refined using first the global interaction data and then user specific interaction data.

By starting with a set of heuristics, the initial users of the system may experience a baseline ranking performance that is then trained by both the global user base and the user's own preferences and selections. The use of both individual and system-wide implicitly collected computer interaction data may provide a greater amount of training data to increase the model accuracy. Depending on the amount of individualized implicitly collected computer interaction data that is obtained, certain implicitly collected computer interaction data may be weighted more heavily in training the model to customize the rankings of the inferences for the user.

The method 500 may further include operation 550 where the methods, systems, machine-readable media, and devices described herein present an indication of the sleep patterns. As shown in FIG. 1, a GUI (e.g., GUI interface 106 in FIG. 1) is produced by a network-based communications application (e.g., GUI component 230 in FIG. 2) of a network-based communications service is shown according to some examples of the present disclosure.

In some forms, the computing system 100 presents suggestions based on the inferences which are generated from the sleep pattern correlations using GUI elements in a personalized suggestion area 110A on the display 104. The computing system 100 may also provide a report to the user of how the various implicitly collected computer interaction data influenced sleep pattern correlation values. In some examples, the GUI elements containing the suggestions may be buttons that fit the personalized suggestion area 110A on the GUI 106. In addition, certain suggestions may potentially be distinguished from the other suggestions in some way (e.g., by highlighting).

In some forms, the personalized suggestion(s) may be delivered through a personal digital assistant (e.g., such as CORTANA® from MICROSOFT®). For example, as shown in FIG. 1, GUI 106 may present a user interface to user 130 via display device 104. User interface may be a graphical depiction of various applications executing on one or more of the client devices 110, such as application 110A (which can be, for example, a web browser) or application 110B (which can be, for example, a media/video player).

Such application(s) can also include or otherwise reflect various content elements. Such content elements can be, for example, alphanumeric characters or strings, words, text, images, media (e.g., video), and/or any other such electronic or digital content that can be displayed, depicted, or otherwise presented via display 104.

As an example, the GUI 106 may present an indication of the sleep patterns to user 130 on one or more of the client devices 110 by passively making a recommendation regarding getting more sleep in general. As another example, the GUI 106 may present an indication of the sleep patterns to user 130 on one or more of the client devices 110 by actively warning a user in specific circumstances where intervention might be more necessary (e.g. alerting via a warning to the user of fatigue prior to driving).

Other forms of the methods, systems, machine-readable media, and devices described herein are contemplated where other types of correlations besides sleep pattern correlations are determined based on the implicitly collected computer interaction data. As an example, the correlations services described herein (see, e.g., correlation services 260, 360 in FIGS. 2 and 3) may analyze the implicitly collected computer interaction data to form correlations and corresponding inferences regarding other types of physiological patterns (individually or collectively. Other example physiological patterns include patterns related to stress, neurodegenerative disorders, cognitive disorders and sleep disorders (beyond just insufficient sleep). Other types of correlations besides the correlations described herein are contemplated.

To protect user privacy, Graphical User Interfaces (GUIs) for user consent and opt-in or opt-out may be provided to allow users to assent to, or restrict, the collection of personal information. In some examples, these GUIs may allow users to delete previously collected information or set restrictions on the types and content of information collected.

Certain embodiments are described herein as including logic or a number of components or mechanisms. Components may constitute either software components (e.g., code embodied on a machine-readable medium) or hardware components. A "hardware component" is a tangible unit capable of performing certain operations and may be configured or arranged in a certain physical manner. In various example embodiments, one or more computer systems (e.g., a standalone computer system, a client computer system, or a server computer system) or one or more hardware components of a computer system (e.g., a processor or a group of processors) may be configured by software (e.g., an application or application portion) as a hardware component that operates to perform certain operations as described herein.

In some embodiments, a hardware component may be implemented mechanically, electronically, or any suitable combination thereof. For example, a hardware component may include dedicated circuitry or logic that is permanently configured to perform certain operations. For example, a hardware component may be a special-purpose processor, such as a Field-Programmable Gate Array (FPGA) or an Application Specific Integrated Circuit (ASIC). A hardware component may also include programmable logic or circuitry that is temporarily configured by software to perform certain operations. For example, a hardware component may include software executed by a general-purpose processor or other programmable processor. Once configured by such software, hardware components become specific machines (or specific components of a machine) uniquely tailored to perform the configured functions and are no longer general-purpose processors. It will be appreciated that the decision to implement a hardware component mechanically, in dedicated and permanently configured circuitry, or in temporarily configured circuitry (e.g., configured by software) may be driven by cost and time considerations.

Accordingly, the phrase "hardware component" should be understood to encompass a tangible record, be that a record that is physically constructed, permanently configured (e.g., hardwired), or temporarily configured (e.g., programmed) to operate in a certain manner or to perform certain operations described herein. As used herein, "hardware-implemented component" refers to a hardware component. Considering embodiments in which hardware components are temporarily configured (e.g., programmed), each of the hardware components need not be configured or instantiated at any one instance in time. For example, where a hardware component comprises a general-purpose processor configured by software to become a special-purpose processor, the general-purpose processor may be configured as respectively different special-purpose processors (e.g., comprising different hardware components) at different times. Software accordingly configures a particular processor or processors, for example, to constitute a particular hardware component at one instance of time and to constitute a different hardware component at a different instance of time.

Hardware components can provide information to, and receive information from, other hardware components. Accordingly, the described hardware components may be regarded as being communicatively coupled. Where multiple hardware components exist contemporaneously, communications may be achieved through signal transmission (e.g., over appropriate circuits and buses) between or among two or more of the hardware components. In embodiments in which multiple hardware components are configured or instantiated at different times, communications between such hardware components may be achieved, for example, through the storage and retrieval of information in memory structures to which the multiple hardware components have access. For example, one hardware component may perform an operation and store the output of that operation in a memory device to which it is communicatively coupled. A further hardware component may then, at a later time, access the memory device to retrieve and process the stored output. Hardware components may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented components that operate to perform one or more operations or functions described herein. As used herein, "processor-implemented component" refers to a hardware component implemented using one or more processors.

Similarly, the methods described herein may be at least partially processor-implemented, with a particular processor or processors being an example of hardware. For example, at least some of the operations of a method may be performed by one or more processors or processor-implemented components. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an API).

The performance of certain of the operations may be distributed among the processors, not only residing within a single machine, but deployed across a number of machines.

In some example embodiments, the processors or processor-implemented components may be located in a single geographic location (e.g., within a home environment, an office environment, or a server farm). In other example embodiments, the processors or processor-implemented components may be distributed across a number of geographic locations.

Some aspects of the subject technology involve collecting personal information about users. It should be noted that the personal information about a user is collected after receiving affirmative consent from the users for the collection and storage of such information. Persistent reminders (e.g., email messages or information displays within an application) are provided to the user to notify the user that his/her information is being collected and stored. The persistent reminders may be provided whenever the user accesses an application or once every threshold time period (e.g., an email message every week). For instance, an arrow symbol may be displayed to the user on his/her mobile device to notify the user that his/her global positioning system (GPS) location is being tracked. Personal information is stored in a secure manner to ensure that no unauthorized access to the information takes place. For example, medical and health related information may be stored in a Health Insurance Portability and Accountability Act (HIPAA) compliant manner.

Example Machine and Software Architecture

The components, methods, applications, and so forth described in conjunction with FIGS. 1-5 are implemented in some embodiments in the context of a machine and an associated software architecture. The sections below describe representative software architecture(s) and machine (e.g., hardware) architecture(s) that are suitable for use with the disclosed embodiments.

Software architectures are used in conjunction with hardware architectures to create devices and machines tailored to particular purposes. For example, a particular hardware architecture coupled with a particular software architecture will create a mobile device, such as a mobile phone, tablet device, or so forth. A slightly different hardware and software architecture may yield a smart device for use in the "internet of things," while yet another combination produces a server computer for use within a cloud computing architecture. Not all combinations of such software and hardware architectures are presented here, as those of skill in the art can readily understand how to implement the inventive subject matter in different contexts from the disclosure contained herein.

Figure 6:
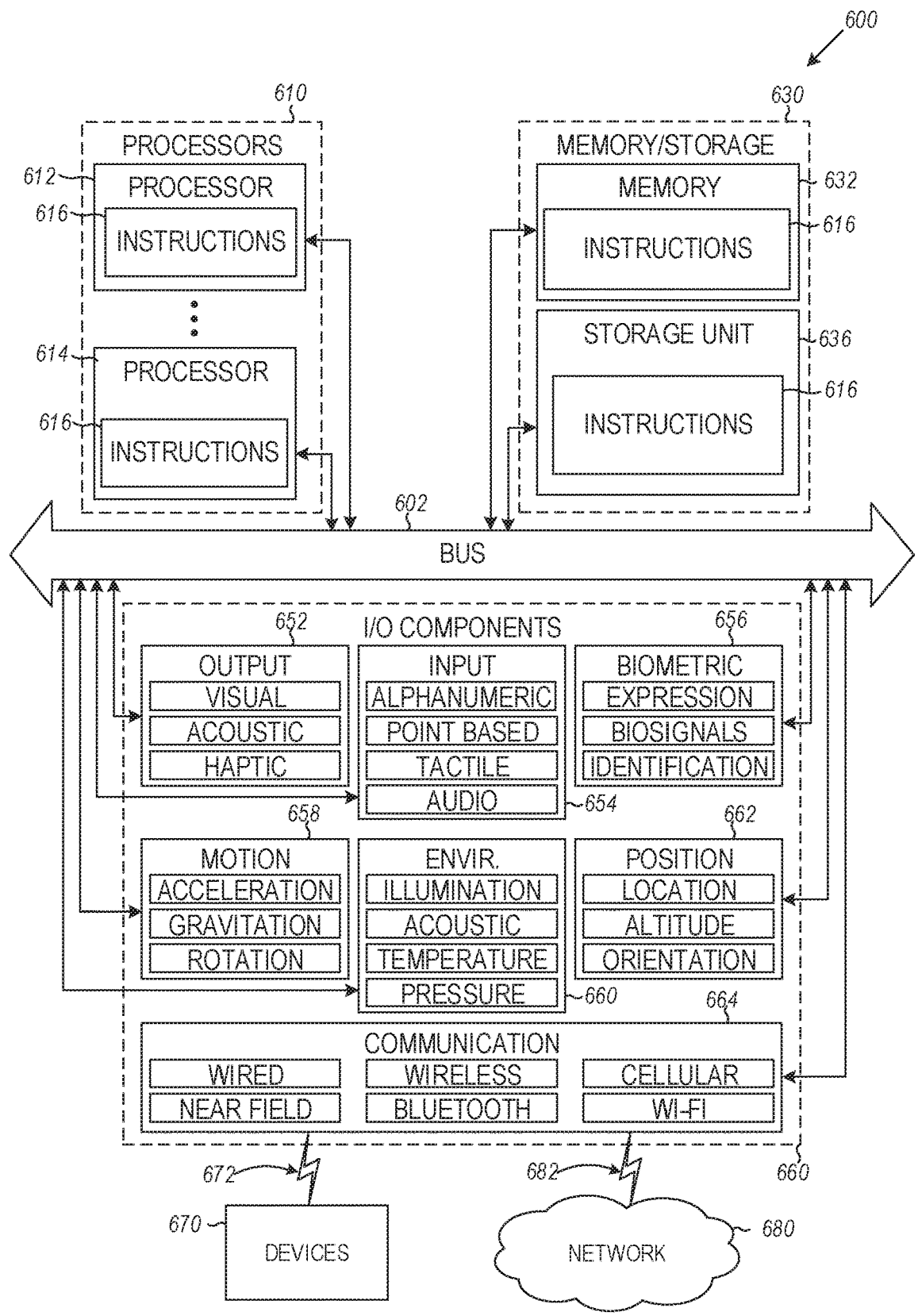
FIG. 6 is a block diagram illustrating components of a machine able to read instructions from a machine-readable medium and perform any of the methodologies discussed herein, in accordance with some embodiments.

FIG. 6 is a block diagram illustrating components of a machine 600, according to some example embodiments, able to read instructions from a machine-readable medium (e.g., a machine-readable storage medium) and perform any one or more of the methodologies discussed herein. Specifically, FIG. 6 shows a diagrammatic representation of the machine 600 in the example form of a computer system, within which instructions 616 (e.g., software, a program, an application, an applet, an app, or other executable code) for causing the machine 600 to perform any one or more of the methodologies discussed herein may be executed. The instructions 616 transform the general, non-programmed machine into a particular machine programmed to carry out the described and illustrated functions in the manner described. In alternative embodiments, the machine 600 operates as a standalone device or may be coupled (e.g., networked) to other machines. In a networked deployment, the machine 600 may operate in the capacity of a server machine or a client machine in a server-client network environment, or as a peer machine in a peer-to-peer (or distributed) network environment. The machine 600 may comprise, but not be limited to, a server computer, a client computer, PC, a tablet computer, a laptop computer, a netbook, a personal digital assistant (PDA), an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 616, sequentially or otherwise, that specify actions to be taken by the machine 600. Further, while only a single machine 600 is illustrated, the term "machine" shall also be taken to include a collection of machines 600 that individually or jointly execute the instructions 616 to perform any one or more of the methodologies discussed herein.

The machine 600 may include processors 610, memory/storage 630, and I/O components 650, which may be configured to communicate with each other such as via a bus 602. In an example embodiment, the processors 610 (e.g., a Central Processing Unit (CPU), a Reduced Instruction Set Computing (RISC) processor, a Complex Instruction Set Computing (CISC) processor, a Graphics Processing Unit (GPU), a Digital Signal Processor (DSP), an ASIC, a Radio-Frequency Integrated Circuit (RFIC), another processor, or any suitable combination thereof) may include, for example, a processor 612 and a processor 614 that may execute the instructions 616. The term "processor" is intended to include multi-core processors that may comprise two or more independent processors (sometimes referred to as "cores") that may execute instructions contemporaneously. Although FIG. 6 shows multiple processors 610, the machine 600 may include a single processor with a single core, a single processor with multiple cores (e.g., a multi-core processor), multiple processors with a single core, multiple processors with multiples cores, or any combination thereof.

The memory/storage 630 may include a memory 632, such as a main memory, or other memory storage, and a storage unit 636, both accessible to the processors 610 such as via the bus 602. The storage unit 636 and memory 632 store the instructions 616 embodying any one or more of the methodologies or functions described herein. The instructions 616 may also reside, completely or partially, within the memory 632, within the storage unit 636, within at least one of the processors 610 (e.g., within the processor's cache memory), or any suitable combination thereof, during execution thereof by the machine 600. Accordingly, the memory 632, the storage unit 636, and the memory of the processors 610 are examples of machine-readable media.

As used herein, "machine-readable medium" means a device able to store instructions (e.g., instructions 616) and data temporarily or permanently and may include, but is not limited to, random-access memory (RAM), read-only memory (ROM), buffer memory, flash memory, optical media, magnetic media, cache memory, other types of storage (e.g., Erasable Programmable Read-Only Memory (EEPROM)), and/or any suitable combination thereof. The term "machine-readable medium" should be taken to include a single medium or multiple media (e.g., a centralized or distributed database, or associated caches and servers) able to store the instructions 616. The term "machine-readable medium" shall also be taken to include any medium, or combination of multiple media, that is capable of storing instructions (e.g., instructions 616) for execution by a machine (e.g., machine 600), such that the instructions, when executed by one or more processors of the machine (e.g., processors 610), cause the machine to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes signals per se.

The I/O components 650 may include a wide variety of components to receive input, provide output, produce output, transmit information, exchange information, capture measurements, and so on. The specific I/O components 650 that are included in a particular machine will depend on the type of machine. For example, portable machines such as mobile phones will likely include a touch input device or other such input mechanisms, while a headless server machine will likely not include such a touch input device. It will be appreciated that the I/O components 650 may include many other components that are not shown in FIG. 6. The I/O components 650 are grouped according to functionality merely for simplifying the following discussion and the grouping is in no way limiting. In various example embodiments, the I/O components 650 may include output components 652 and input components 654.

The output components 652 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth.

The input components 654 may include alphanumeric input components (e.g., a keyboard, a touch screen configured to receive alphanumeric input, a photo-optical keyboard, or other alphanumeric input components), point based input components (e.g., a mouse, a touchpad, a trackball, a joystick, a motion sensor, or another pointing instrument), tactile input components (e.g., a physical button, a touch screen that provides location and/or force of touches or touch gestures, or other tactile input components), audio input components (e.g., a microphone), and the like.

In further example embodiments, the I/O components 650 may include biometric components 656, motion components 658, environmental components 660, or position components 662, among a wide array of other components. For example, the biometric components 656 may include components to detect expressions (e.g., hand expressions, facial expressions, vocal expressions, body gestures, or eye tracking), measure bio signals (e.g., blood pressure, heart rate, body temperature, perspiration, or brain waves), measure exercise-related metrics (e.g., distance moved, speed of movement, or time spent exercising) identify a person (e.g., voice identification, retinal identification, facial identification, fingerprint identification, or electroencephalogram based identification), and the like. The motion components 658 may include acceleration sensor components (e.g., accelerometer), gravitation sensor components, rotation sensor components (e.g., gyroscope), and so forth.

The environmental components 660 may include, for example, illumination sensor components (e.g., photometer), temperature sensor components (e.g., one or more thermometers that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detect concentrations of hazardous gases for safety or to measure pollutants in the atmosphere), or other components that may provide indications, measurements, or signals corresponding to a surrounding physical environment.

The position components 662 may include location sensor components (e.g., a Global Position System (GPS) receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 650 may include communication components 664 operable to couple the machine 600 to a network 680 or devices 670 via a coupling 682 and a coupling 672, respectively. For example, the communication components 664 may include a network interface component or other suitable device to interface with the network 680. In further examples, the communication components 664 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 670 may be another machine or any of a wide variety of peripheral devices (e.g., a peripheral device coupled via a USB).

Moreover, the communication components 664 may detect identifiers or include components operable to detect identifiers. For example, the communication components 664 may include Radio Frequency Identification (RFID) tag reader components, NFC smart tag detection components, optical reader components, or acoustic detection components (e.g., microphones to identify tagged audio signals). In addition, a variety of information may be derived via the communication components 664, such as location via Internet Protocol (IP) geolocation, location via Wi-Fi® signal triangulation, location via detecting an NFC beacon signal that may indicate a particular location, and so forth.

In various example embodiments, one or more portions of the network 680 may be an ad hoc network, an intranet, an extranet, a virtual private network (VPN), a local area network (LAN), a wireless LAN (WLAN), a WAN, a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, the network 680 or a portion of the network 680 may include a wireless or cellular network and the coupling 682 may be a Code Division Multiple Access (CDMA) connection, a Global System for Mobile communications (GSM) connection, or another type of cellular or wireless coupling. In this example, the coupling 682 may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE)

standard, others defined by various standard-setting organizations, other long range protocols, or other data transfer technology.

The instructions 616 may be transmitted or received over the network 680 using a transmission medium via a network interface device (e.g., a network interface component included in the communication components 664) and utilizing any one of a number of well-known transfer protocols (e.g., HTTP). Similarly, the instructions 616 may be transmitted or received using a transmission medium via the coupling 672 (e.g., a peer-to-peer coupling) to the devices 670. The term "transmission medium" shall be taken to include any intangible medium that is capable of storing, encoding, or carrying the instructions 616 for execution by the machine 600, and includes digital or analog communications signals or other intangible media to facilitate communication of such software.

What is claimed is:

1. A method for improving performance based on sleep patterns, the method including at least one processor performing steps comprising:
   receiving implicitly collected computer interaction data of a user from a computing device, the implicitly collected computer interaction data collected during the user's interaction with the computing device;
   accessing a data store of previously collected computer interaction data, the previously collected computer interaction data correlated with sleep patterns of at least one of the user and other users;
   comparing the users implicitly collected computer interaction data to the previously collected computer interaction data;
   inferring the user's sleep pattern based on the comparing using an inference model; and
   presenting a suggestion to the user via at least one of an audio and a visual interface of the computing device based on the user's sleep pattern to adapt the user's experience with the computing device by making the user aware of the user's sleep pattern.

2. The method of claim 1, wherein delivering a suggestion to the user includes delivering at least one of a content suggestion that provides information to the user about how the user can improve sleep patterns and an action suggestion.

3. The method of claim 2, wherein delivering an action suggestion to the user includes scheduling at least one task for the user.

4. The method of claim 2, wherein delivering an action suggestion to the user includes sending a reminder to the user about a scheduled task.

5. The method of claim 4, wherein providing information to the user includes providing information related to at least one of diet, exercise, relaxation and stress.

6. The method of claim 4, wherein providing information to the user includes showing at least one of a document, video clip, audio clip and picture.

7. The method of claim 1, wherein delivering a suggestion to the user based on the inferring includes ranking a plurality of suggestions based on the inferring and delivering the highest ranking suggestion to the user.

8. The method of claim 7, wherein ranking the plurality of suggestions includes modifying the inferring of the user's sleep pattern based on feedback received from the user relative to the previously delivered suggestion and reranking the plurality of suggestions.

9. The method of claim 7, wherein ranking the plurality of suggestions includes monitoring the user's interaction with at least one previously delivered suggestion.

10. The method of claim 1, wherein the implicitly collected computer interaction data comprises at least one of user mouse cursor activity, audio inputs from the user, visual images of the user, inputs from a tracking component of the computing device, keyboard inputs by the user, touch screen inputs by the user, click interactions by the user with a computer application, and online computer interactions by the user.

11. A non-transitory computer readable medium comprising instructions, which when executed by at least one processor, configure the processor to perform operations for improving performance based on sleep patterns comprising:
    receiving implicitly collected computer interaction data of a user from a computing device, the implicitly collected computer interaction data collected during the user's interaction with the computing device;
    accessing a data store of previously collected computer interaction data, the previously collected computer interaction data correlated with sleep patterns of at least one of the user and other users;
    comparing the users implicitly collected computer interaction data to the previously collected computer interaction data;
    inferring the user's sleep pattern based on the comparing using an inference model; and
    presenting a suggestion to the user via at least one of an audio and a visual interface of the computing device based on the user's sleep pattern to adapt the user's experience with the computing device by making the user aware of the user's sleep pattern.

12. The non-transitory computer readable medium of claim 11, wherein delivering a suggestion to the user includes delivering at least one of a content suggestion that provides information to the user about the user can improve sleep patterns and an action suggestion, wherein delivering an action suggestion to the user includes scheduling at least one task for the user, wherein delivering an action suggestion to the user includes sending a reminder to the user about a scheduled task.

13. The non-transitory computer readable medium of claim 12, wherein providing information to the user includes providing information related to at least one of diet, exercise, relaxation and stress.

14. The non-transitory computer readable medium of claim 11, wherein delivering a suggestion to the user based on the inferring includes ranking a plurality of suggestions based on the inferring and delivering the highest ranking suggestion to the user, wherein ranking the plurality of suggestions includes modifying the inferring of the user's sleep pattern based on feedback received from the user relative to the previously delivered suggestion and reranking the plurality of suggestions, wherein ranking the plurality of suggestions includes monitoring the user's interaction with at least one previously delivered suggestion.

15. The non-transitory computer readable medium of claim 11, wherein the implicitly collected computer interaction data comprises at least one of user mouse cursor activity, audio inputs from the user, visual images of the user, inputs from a tracking component of the computing device, keyboard inputs by the user, touch screen inputs by the user, click interactions by the user with a computer application, and online computer interactions by the user.

16. A system for improving performance based on sleep patterns comprising:
    at least one processor;

a storage device comprising instructions, which when executed by the at least one processor, configure the processor to perform operations comprising:

receiving implicitly collected computer interaction data of a user from a computing device, the implicitly collected computer interaction data collected during the user's interaction with the computing device;

accessing a data store of previously collected computer interaction data, the previously collected computer interaction data correlated with sleep patterns of at least one of the user and other users;

comparing the users implicitly collected computer interaction data to the previously collected computer interaction data;

inferring the user's sleep pattern based on the comparing using an inference model; and presenting a suggestion to the user via at least one of an audio and a visual interface of the computing device based on the user's sleep pattern to adapt the user's experience with the computing device by making the user aware of the user's sleep pattern.

17. The system of claim 16, wherein delivering a suggestion to the user includes delivering at least one of a content suggestion that provides information to the user about the user can improve sleep patterns and an action suggestion, wherein delivering an action suggestion to the user includes scheduling at least one task for the user, wherein delivering an action suggestion to the user includes sending a reminder to the user about a scheduled task.

18. The system of claim 17, wherein providing information to the user includes providing information related to at least one of diet, exercise, relaxation and stress.

19. The system of claim 16, wherein delivering a suggestion to the user based on the inferring includes ranking a plurality of suggestions based on the inferring and delivering the highest ranking suggestion to the user, wherein ranking the plurality of suggestions includes modifying the inferring of the user's sleep pattern based on feedback received from the user relative to the previously delivered suggestion and reranking the plurality of suggestions, wherein ranking the plurality of suggestions includes monitoring the user's interaction with at least one previously delivered suggestion.

20. The system of claim 16, wherein the implicitly collected computer interaction data comprises at least one of user mouse cursor activity, audio inputs from the user, visual images of the user, inputs from a tracking component of the computing device, keyboard inputs by the user, touch screen inputs by the user, click interactions by the user with a computer application, and online computer interactions by the user.

* * * * *